United States Patent
Schweinsberg

(10) Patent No.: US 9,168,217 B2
(45) Date of Patent: *Oct. 27, 2015

(54) GENTLE OXIDATIVE HAIR TREATMENT WITH OXIDIZING AGENT AND SPECIAL STARCH DERIVATIVE

(71) Applicant: Henkel AG & Co. KGaA, Düsseldorf (DE)

(72) Inventor: Matthias Schweinsberg, Hamburg (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/303,131

(22) Filed: Jun. 12, 2014

(65) Prior Publication Data

US 2014/0290686 A1 Oct. 2, 2014

Related U.S. Application Data

(63) Continuation of application No. PCT/EP2012/071818, filed on Nov. 5, 2012.

(30) Foreign Application Priority Data

Dec. 13, 2011 (DE) .......................... 10 2011 088 398

(51) Int. Cl.

| | |
|---|---|
| *A61Q 5/10* | (2006.01) |
| *A61K 8/81* | (2006.01) |
| *A61K 8/73* | (2006.01) |
| *A61Q 5/08* | (2006.01) |
| *A61K 8/22* | (2006.01) |
| *A45D 7/04* | (2006.01) |
| *A61Q 5/00* | (2006.01) |

(52) U.S. Cl.
CPC ................. *A61K 8/8111* (2013.01); *A45D 7/04* (2013.01); *A61K 8/22* (2013.01); *A61K 8/732* (2013.01); *A61Q 5/00* (2013.01); *A61Q 5/08* (2013.01); *A61Q 5/10* (2013.01)

(58) Field of Classification Search
CPC ........... A61Q 5/10; A61Q 5/004; A61K 8/22; A61K 8/732
USPC ...................................... 8/405, 406, 408, 552
See application file for complete search history.

(56) References Cited

U.S. PATENT DOCUMENTS

| | | | |
|---|---|---|---|
| 5,871,756 A | 2/1999 | Jeffcoat et al. | |
| 8,603,447 B2 * | 12/2013 | Mueller et al. | 424/70.11 |
| 8,609,078 B2 * | 12/2013 | Schweinsberg et al. | 424/70.13 |
| 8,790,628 B2 * | 7/2014 | Schweinsberg et al. | 424/70.13 |
| 2004/0078905 A1 * | 4/2004 | Terranova et al. | 8/405 |
| 2004/0234486 A1 * | 11/2004 | Hashimoto | 424/70.16 |
| 2005/0193501 A1 | 9/2005 | Chan et al. | |
| 2006/0075580 A1 | 4/2006 | Chan et al. | |
| 2012/0207695 A1 * | 8/2012 | Schweinsberg et al. | 424/70.13 |
| 2012/0328532 A1 * | 12/2012 | Schweinsberg et al. | 424/47 |

FOREIGN PATENT DOCUMENTS

| | | |
|---|---|---|
| DE | 2359399 | 6/1975 |
| DE | 3843892 | 6/1990 |
| DE | 4133957 A | 4/1993 |
| DE | 19543988 | 5/1997 |
| DE | 19756454 | 6/1999 |
| DE | 102004002349 A1 | 8/2005 |
| EP | 740931 | 11/1996 |
| EP | 0948960 A2 | 10/1999 |
| EP | 998908 A2 | 5/2000 |
| EP | 1568351 A1 | 8/2005 |
| EP | 1669104 A2 | 6/2006 |
| GB | 1026978 | 4/1966 |
| GB | 1153196 | 5/1969 |
| JP | 02019576 A1 | 1/1990 |
| JP | H0517322 A | 1/1993 |
| JP | 2010215599 A | 9/2010 |
| WO | 9408969 | 4/1994 |
| WO | 9408970 | 4/1994 |
| WO | 9615765 | 5/1996 |
| WO | 9801109 A1 | 1/1998 |
| WO | 2005082321 A1 | 9/2005 |
| WO | 2012084904 A1 | 6/2012 |

OTHER PUBLICATIONS

Singh et al, Factors influencing the physico-chemical, morphological, thermal and rheological properties of some chemically modified starches for food applications—A review, Food Hydrocolloids 21, Jan. 1, 2007, pp. 1-22, Food Hydrocolloids, Elsevier BV, NL, Bd. 21, Nr, www.elsevier.com/locate/foodhyd.

Database WPI, Week 201067, Thomson Scientific, London, GB; AN 2010-M48909, XP2728050, & JP 2010 215599 A (MANDOM KK), 30. Sep. 30, 2010; pp. 1-2.

Saowakon Wattanachant et al: "Effect of crosslinking reagents and hydroxypropylation levels on dual-modified sago starch properties", Food Chemistry 80, Apr. 1, 2003, pp. 463-471, www.elsevier.com/locate/foodchem, XP55132395, ISSN: 0308-8146, 001:10.1016/S0308-8146(02)00314-X.

* cited by examiner

*Primary Examiner* — Eisa Elhilo

(74) *Attorney, Agent, or Firm* — Steven L. Nichols; Van Cott, Bagley, Cornwall & McCarthy P.C.

(57) ABSTRACT

The present specification provides for an oxidative hair treatment agent. The agent includes, in a cosmetic carrier, a combination of at least one oxidizing agent and at least one modified starch. The modified starch is modified by propylene oxide, has an average molecular weight between 50 and 2500 kiloDaltons (kDa), and has a propylene oxide content between 0.1 and 20.0 weight percent (wt %) based on the weight of the modified starch.

19 Claims, No Drawings

GENTLE OXIDATIVE HAIR TREATMENT WITH OXIDIZING AGENT AND SPECIAL STARCH DERIVATIVE

RELATED DOCUMENTS

The present specification is a U.S. continuation patent application under 35 U.S.C. 111(a) and claims the right of priority under 35 U.S.C. 365 to international patent Application No. PCT/EP2012/071818, filed Nov. 5, 2012, entitled "Gentle Oxidative Hair Treatment with Oxidizing Agent and Special Starch Derivative" which claims benefit of German application No.: 102011088398.3, filed Dec. 13, 2011, these applications are herein incorporated by reference in their entirety.

FIELD OF THE INVENTION

The present application generally relates to the cosmetic use of a special starch, modified by means of propylene oxide, during oxidative hair treatment in order to decrease hair damage. A corresponding method for oxidative hair treatment, as well as the agents usable therein are also a subject of the present specification.

BACKGROUND OF THE INVENTION

Human hair is treated with hair-cosmetic preparations in many ways. These preparations include, for example, cleaning the hair with shampoo, care and regeneration with rinses and therapies, bleaching, coloring, and deforming the hair using coloring agents, tinting agents, waving agents, and styling preparations.

Permanent oxidative coloring, as well as hair bleaching and retention in the context of permanent waving, may be performed as an oxidative hair treatment in the presence of oxidizing agents such as hydrogen peroxide. Unfortunately, the oxidizing agent in this context not only achieves the desired cosmetic effect, but also damages the structure of the hair keratin. This causes the cysteine present in keratin to be oxidized to cysteic acid, which has a negative effect on the stability, haptics, and appearance of the hair fibers. Hair damaged in this way looks dull and brittle. In extreme cases, hair breakage can even occur.

European patent application EP 1568351 A1 to Vona Jr. discloses the use of a composition, comprising a starch including pregelatinized amylose, to preserve artificial color on hair.

International patent application WO 1998001109 A1 to Mueller et al. relates to agents for cleaning or caring for hair, the agent including a pregelatinized crosslinked starch selected from a ($C_2$ to $C_6$) hydroxyalkyl starch and a ($C_2$ to $C_6$) acyl starch.

The object of the present specification is to decrease the above-described side effects of oxidative hair treatments during the oxidative hair treatment itself, without degrading the efficiency of the oxidative cosmetic especially in terms of color intensity, color fastness, lightening performance, or waving effect.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

The present specification describes an oxidative hair treatment agent. The agent includes, in a cosmetic carrier a combination of at least one oxidizing agent and at least one modified starch. The modified starch is modified by propylene oxide, has an average molecular weight between 50 and 2500 kiloDaltons (kDa), and has a propylene oxide content between 0.1 and 20.0 weight percent (wt %) based on the weight of the modified starch.

The present specification describes a method for providing an oxidative treatment to hair. The method includes applying at least one oxidative cosmetic agent onto hair. The oxidative cosmetic agent comprises, in a cosmetic carrier, at least one oxidizing agent. The method also includes rinsing the oxidative cosmetic agent out of the hair after a contact time. The method also includes at least one of 1) immediately before application of the at least one oxidative cosmetic agent, applying and rinsing a cosmetic agent from the hair, in which the cosmetic agent comprises, in a cosmetic carrier, at least one modified starch having an average molecular weight between 50 and 2500 kiloDaltons (kDa) and a propylene oxide content between 0.1 and 20.0 wt % and 2) adding the at least one modified starch into the oxidative cosmetic agent.

The present specification describes a method for using at least one modified starch to decrease oxidative hair damage in the context of an oxidative hair treatment. The method includes applying the at least one modified starch to hair. The modified starch is modified by propylene oxide, has an average molecular weight between 50 and 2500 kDa, and has a propylene oxide content between 0.1 and 20.0 wt %. The method also includes rinsing the modified starch from the hair.

DETAILED DESCRIPTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found that the object is achieved to an outstanding degree by the use of at least one starch, modified by means of propylene oxide, that has an average molecular weight (weight-average) from 50 to 2500 kDa, and a propylene oxide content from 0.1 to 20.0 wt % (based on the weight of the starch modified by means of propylene oxide). The effect is produced during the oxidative hair treatment.

A first subject of the present specification is therefore the cosmetic use of at least one starch, modified by means of propylene oxide, that has an average molecular weight (weight-average) from 50 to 2500 kDa and a propylene oxide content from 0.1 to 20.0 wt % (based on the weight of the starch modified by means of propylene oxide), to decrease oxidative hair damage in the context of an oxidative hair treatment.

The reduction in oxidative hair damage is expressed in particular as improved combability of the hair, and/or hair shine. These effects result using either simultaneous or directly subsequent oxidative hair treatment.

As used in the present specification and in the appended claims, an "oxidative hair treatment" refers to the action on hair of an oxidative cosmetic agent including, in a cosmetic carrier, at least one oxidizing agent.

The oxidizing agents for purposes of the present specification are different from atmospheric oxygen and possess an oxidation potential, making it possible to create disulfide bridges within or between the proteins of the hair keratin, and/or to oxidatively lighten the natural hair pigment melanin, and/or to oxidize an oxidation dye precursor of the developer type.

Relevant oxidizing agents are preferably hydrogen peroxide and/or at least one addition product thereof, in particular with inorganic or organic compounds, for example sodium perborate, sodium percarbonate, magnesium percarbonate, sodium percarbamide, polyvinylpyrrolidone·nH$_2$O$_2$ (n being a positive integer greater than 0), urea peroxide, and melamine peroxide.

According to the present specification the oxidative cosmetic agent may also be applied onto the hair together with a catalyst that activates oxidation of the substrate, for example oxidation dye precursors or melanin. Such catalysts are, for example, metal ions, iodides, quinones, or specific enzymes.

Suitable metal ions are, for example Zn$^{2+}$, Cu$^{2+}$, Fe$^{2+}$, Fe$^{3+}$, Mn$^{2+}$, Mn$^{4+}$, Li$^+$, Mg$^{2+}$, Ca$^{2+}$, and Al$^{3+}$. Further, Zn$^{2+}$, Cu$^{2+}$, and Mn$^{2+}$ are particularly suitable in this context. The metal ions may be used, in principle, in the form of any physiologically acceptable salt or in the form of a complexed compound. Preferred salts are acetates, sulfates, halides, lactates, and tartrates. The use of these metal salts makes it possible both to accelerate formation of a color and to influence the color tint in a controlled fashion.

Suitable enzymes are, for example, peroxidases that may appreciably intensify the action of small quantities of hydrogen peroxide. Also suitable according to the present specification are those enzymes which generate small quantities of hydrogen peroxide in situ with the aid of atmospheric oxygen and in that fashion biocatalytically activate oxidation of the dye precursors. Particularly suitable catalysts for the oxidation of dye precursors are the so-called two-electron oxidoreductases in combination with the substrates specific to them, e.g. pyranose oxidase and, for example, D-glucose and galactose; glucose oxidase and D-glucose; glycerol oxidase and glycerol; pyruvate oxidase and pyruvic acid or salts thereof; alcohol oxidase and alcohol (MeOH, EtOH); lactate oxidase and lactic acid and salts thereof; tyrosinase oxidase and tyrosine; uricase and uric acid or salts thereof; choline oxidase and choline; and amino acid oxidase and amino acids.

The oxidizing agent is included in the oxidative cosmetic agent preferably in a quantity from 1.0 to 10.0 wt %, in particular from 3.0 to 10.0 wt %, based in each case on the weight of the agent.

The at least one starch modified by propylene oxide is preferably used immediately before or during the oxidative hair treatment, in the form of an agent including, in a cosmetic carrier, at least one modified starch, modified by means of propylene oxide, that has an average molecular weight (weight-average) from 50 to 2500 kDa and a propylene oxide content from 0.1 to 20.0 wt % (based on the weight of the starch modified by means of propylene oxide).

As used in the present specification and in the appended claims, utilization "immediately before" the oxidative hair treatment refers to a use that is followed directly by the oxidative hair treatment, wherein the agent including the modified starch has previously been rinsed off the hair or preferably been left on the hair, and the hair preferably is still wet or at least possesses palpable residual moisture. Examples of suitable pretreatment agents are to be gathered from the Examples section of this application.

Starch is a reserve carbohydrate that is stored by many plants in the form of starch grains (granules), usually 1 to 200 micrometers (μm) in size, in various parts of the plant, for example in tubers or roots, cereal seeds, fruits, and in the pith. A starch modified by means of propylene oxide that is usable according to the present specification is derived preferably from at least one starch from potatoes, corn, rice, peas, acorns, chestnuts, barley, wheat, bananas, sago, millet, sorghum, oats, barley, rye, beans, yams, arrowroot or cassava. Particularly pronounced effects according to the present specification are achieved with corresponding tapioca starch modified by means of propylene oxide, potato starch modified by means of propylene oxide, corn starch modified by means of propylene oxide, or mixtures thereof. It is very particularly preferred according to the present specification to use tapioca starch modified by means of propylene oxide as a corresponding starch modified by means of propylene oxide.

Starch belongs to the homoglycan family and is a polycondensation product of D-glucose. Starch is made up of three structurally different polymers of d-glucopyranose, namely amylose, amylopectin, and a so-called intermediate fraction. Higher plants include between 0 and 45 wt % amylose, based on dry substance.

The intermediate fraction, which is also referred to as "anomalous amylopectin," is structurally intermediate between amylose and amylopectin. The quantitative indications defined in the context of this Application for amylopectin include the intermediate fraction.

It is preferred according to the present specification if the starch modified by means of propylene oxide possesses an amylose content of less than 25 wt %, in particular less than 20 wt %, based in each case on the weight of said starch, It has been found that a starch that includes 17 to 22 wt % amylose and 78 to 83 wt % amylopectin is particularly suitable for achieving the effect according to the present specification.

Amylose is made up of predominantly linearly α-1,4-glycosidically linked d-glucose, M$_r$ 50,000 to 150,000. The resulting chains form double helices in the starch.

Amylopectin also includes, besides the α-1,4 links described for amylose, α-1,6 bonds (in a quantity from 4 to 6%) as branching points. The average spacing between the branching points is approximately 12 to 17 glucose units. The molar mass of 10$^7$ to 7*10$^8$ corresponds to approximately 10$^5$ glucose units, making amylopectin one of the largest biopolymers. The aforesaid branching points are distributed over the molecule in such a way that a bundle structure, with relatively short side chains, develops. Each double helix is formed by two of these side chains. As a result of the many branching points, amylopectin is relatively easily soluble in water.

As used in the present specification and in the appended claims, a "starch modified by means of propylene oxide," "a modified starch," "a starch modified by propylene oxide" or similar terminology is understood according to the present specification as a reaction product of a starch with propylene oxide. A reaction product of this kind comprises at least one structural unit of formula (I)

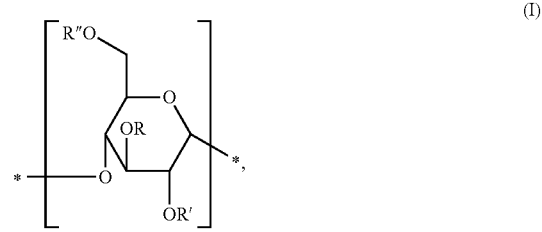

(I)

in which at least one residue R, R', or R" denotes a group of the formula

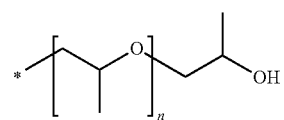

where n≥0,
and at most two of the residues from among R, R', R" denote a hydrogen atom. In formulas of the present application, a bond identified with the * symbol corresponds to a free valence of the corresponding structural unit. The corresponding starches modified by means of propylene oxide are made available, for example, by reacting a natural starch with propylene oxide. Before modification by means of propylene oxide, the starch can have been exposed to a variety of physical or chemical processes, for example a heat treatment, shear, a thermal, acid-hydrolytic, oxidizing, or enzymatic cleavage, etc.

It is preferred according to the present specification if the starch modified by means of propylene oxide is not present in the agent according to the present specification in the form of individual starch grains (granules). For this purpose the starch grains are disintegrated, for example by heat or shear, and the corresponding polysaccharide molecules are released from the network. The released polysaccharide molecules are modified by means of propylene oxide after or before release.

In the context of a preferred example, the starch modified by means of propylene oxide is gelatinized. When an aqueous suspension of starch is heated or compressed, a tangential swelling of the bodies is then observed at a critical temperature or pressure, with loss of birefringence, a change in X-ray structure, and an abrupt rise in the viscosity of the solution. This phenomenon is called "gelatinization."

The starches according to the present specification modified by means of propylene oxide are present in the agent according to the present specification in a molecular weight distribution. The molecular weight distribution was determined experimentally by gel filtration chromatography against dextran. An important feature of the present specification is the weight average of the average molecular weight of the starches, modified by means of propylene oxide, included in the agent according to the present specification. The aforesaid weight average is an average molecular weight that takes into account the total weight of the molecules of various molecular weights, and not simply the number of molecules. For statistical calculation of the weight average, firstly the "weight break" is defined by Formula (1) as given below.

$$w_i = (N_i M_i)/[\Sigma(N_i M_i)] \quad \text{Formula (1).}$$

Formula (1) indicates the weight proportion, in the sample, of macromolecules that are made up of i segments (e.g. monomer modules) of mass $M_i$ and that occur $N_i$ times in the sample. The weight average of the molecular weight $M_w = \Sigma w_i M_i$ is thus given by Formula (2) as given below.

$$M_w = [\Sigma(N_i M_i^2)]/[\Sigma(N_i M_i)] \quad \text{Formula (2).}$$

Particularly preferred agents according to the present specification include those aforesaid starches modified by means of propylene oxide which have an average molecular weight (weight-average) from 100 to 2000 kDa, in particular from 500 to 1800 kDa, very particularly preferably from 700 to 1000 kDa.

It is particularly preferred according to the present specification if the starch modified by means of propylene oxide, or modified starch, is uncrosslinked. Crosslinking of the starch modified by means of propylene oxide exists when the linear or branched polysaccharide macromolecules of the starch are linked covalently by means of a crosslinking agent, forming a three-dimensional, insoluble, and only swellable polymeric network. Natural starch is generally considered uncrosslinked and if crosslinking were desirable, requires artificial crosslinking by means of synthesis chemistry. Artificial crosslinking of this kind can be carried out using crosslinking agents, for example epichlorohydrin. Starches (modified by means of propylene oxide) that do not exhibit such crosslinking are uncrosslinked.

To achieve a lower molecular weight, for example from 700 to 900 kDa, the aforesaid starches are preferably exposed to a mechanical cleavage, enzymatic cleavage (in particular using alpha-amylase, beta-amylase, glucoamylase, or debranching enzymes), acid-hydrolytic cleavage (in particular using hydrochloric acid, sulfuric acid, or phosphoric acid), thermal cleavage, or a reaction with oxidizing agents (such as periodate, hypochlorite, chromic acid, permanganate, nitrogen dioxide, hydrogen peroxide, or organic percarboxylic acid, preferably with hydrogen peroxide). Kneaders, extruders, stator/rotor machines, and/or agitators are suitable for mechanical cleavage of the starch.

Oxidative cleavage by means of hydrogen peroxide is preferably suitable. For this purpose, for example, the starch modified by means of propylene oxide is added to water, heated to 50 to 70° C., hydrogen peroxide is added, and stirring occurs at 70 to 85° C. for 2 to 5 hours.

The propylene oxide content of the starch affects fine-tuning of the properties of the hair protection obtained, and the stability of the cosmetic agents. The parameters can be further optimized if the aforesaid starch modified by means of propylene oxide has, based on the weight of the modified starch, a propylene oxide content from 2 to 12 wt %, particularly preferably a propylene oxide content from 3.0 to 10.0 wt %, very particularly preferably a propylene oxide content from 4.0 to 6.0 wt %. The propylene oxide content can be determined, for example, after carrying out a Hodges cleavage, using the method according to German Institute for Standardization standard "DIN EN 13268."

Those cosmetic agents in which the aforesaid starch modified by means of propylene oxide has, in a 43-wt % solution in water (i.e. in a 43-wt % aqueous solution), a viscosity in the range from 150 to 1,500,000 millipascal-seconds (mPa·s) (as measured by a Brookfield viscometer, spindle 7 at 20 degrees Celsius (° C.) and at 20 rotations per minute (rpm)) are outstandingly suitable for purposes of the present specification. Outstandingly suitable propylene-oxide-modified polysaccharides have viscosities from 3000 to 200,000 mPa·s, in particular from 10,000 to 100,000 mPa·s, very particularly preferably from 40,000 to 70,000 mPa·s (measured in each case under the conditions recited above).

The aforesaid starch modified by means of propylene oxide is used preferably in a cosmetic carrier. Suitable cosmetic carriers according to the present specification are in particular creams, emulsions, gels, or also surfactant-containing foaming solutions such as shampoos, foam aerosols, or other preparations that are suitable in particular for utilization on hair. It is also conceivable, however, to integrate the ingredients into a powdered or also tablet-shaped formulation that is dissolved in water before use. The cosmetic carriers can in particular be aqueous or aqueous alcoholic. As used in the present specification and in the appended claims, an "aqueous" cosmetic carrier includes at least 50 wt % water. Further, as used in the present specification and in the appended claims an "aqueous alcoholic" cosmetic carriers refers to aqueous solutions including 3 to 70 wt % of a $C_1$ to $C_4$ alcohol, in particular ethanol or isopropanol. The agents according to the present specification may additionally include further organic solvents, for example methoxybutanol, benzyl alcohol, ethyl diglycol, or 1,2-propylene glycol. All water-soluble organic solvents are preferred in this context.

In a context of simultaneous use of the oxidative cosmetic agent and a cosmetic agent including the aforesaid starch modified by means of propylene oxide, the two agents can be mixed with one another, optionally, only immediately before utilization, or can be applied successively onto the hair without an intermediate rinsing step. In a preferred example, the oxidative cosmetic agent used according to the present specification therefore additionally includes the aforesaid starch modified by means of propylene oxide.

A second subject of the present specification is therefore cosmetic agents including, in a cosmetic carrier, a combination of at least one oxidizing agent and at least one starch modified by means of propylene oxide. The modified starch has an average molecular weight (weight-average) from 50 to 2500 kDa and a propylene oxide content from 0.1 to 20.0 wt % (based on the weight of the starch modified by means of propylene oxide). Corresponding starches modified by means of propylene oxide, and preferred representatives thereof, have already been recited in the context of the statements regarding the first subject of the present specification. Preferred cosmetic carriers are those of the first subject of the present specification. Corresponding oxidizing agents, and preferred representatives thereof, have likewise been defined in the context of the first subject of the present specification.

Cosmetic agents very particularly preferred according to the present specification conform to at least one of the examples A) to R).

A): A cosmetic agent for coloring keratinic fibers, in particular human hair, including in a cosmetic carrier at least one oxidizing agent and at least one uncrosslinked starch, modified by means of propylene oxide, that has an average molecular weight (weight-average) from 50 to 2500 kDa and a propylene oxide content from 2.0 to 12.0 wt % (based on the weight of the starch modified by means of propylene oxide).

B): A cosmetic agent for coloring keratinic fibers, in particular human hair, including in a cosmetic carrier at least one oxidizing agent and at least one starch, modified by means of propylene oxide, that has an average molecular weight (weight-average) from 700 to 1000 kDa and a propylene oxide content from 2.0 to 12.0 wt % (based on the weight of the starch modified by means of propylene oxide).

C): A cosmetic agent for coloring keratinic fibers, in particular human hair, including in a cosmetic carrier at least one oxidizing agent and at least one starch, modified by means of propylene oxide, that has an average molecular weight (weight-average) from 50 to 2500 kDa, a propylene oxide content from 2.0 to 12.0 wt % (based on the weight of the starch modified by means of propylene oxide), and a viscosity from 3000 to 200,000 mPas (in 43-wt % aqueous solution, Brookfield viscometer, spindle 7, at 20° C. and 20 rpm).

D): A cosmetic agent for coloring keratinic fibers, in particular human hair, including in a cosmetic carrier at least one oxidizing agent and at least one starch, modified by means of propylene oxide, that has an average molecular weight (weight-average) from 50 to 2500 kDa, a propylene oxide content from 2.0 to 12.0 wt % (based on the weight of the starch modified by means of propylene oxide), and a viscosity from 1000 to 100,000 mPas (in 43-wt % aqueous solution, Brookfield viscometer, spindle 7, at 20° C. and 20 rpm).

E): A cosmetic agent for coloring keratinic fibers, in particular human hair, including in a cosmetic carrier at least one oxidizing agent and at least one starch, modified by means of propylene oxide, that has an average molecular weight (weight-average) from 700 to 1000 kDa, a propylene oxide content from 2.0 to 12.0 wt % (based on the weight of the starch modified by means of propylene oxide), and a viscosity from 3000 to 200,000 mPas (in 43-wt % aqueous solution, Brookfield viscometer, spindle 7, at 20° C. and 20 rpm).

F): A cosmetic agent for coloring keratinic fibers, in particular human hair, including in a cosmetic carrier at least one oxidizing agent and at least one starch, modified by means of propylene oxide, that has an average molecular weight (weight-average) from 700 to 1000 kDa, a propylene oxide content from 2.0 to 12.0 wt % (based on the weight of the starch modified by means of propylene oxide), and a viscosity from 10,000 to 100,000 mPas (in 43-wt % aqueous solution, Brookfield viscometer, spindle 7, at 20° C. and 20 rpm).

G): A cosmetic agent for coloring keratinic fibers, in particular human hair, including in a cosmetic carrier at least one oxidizing agent and at least one uncrosslinked starch, modified by means of propylene oxide, selected from tapioca starch, potato starch, corn starch, or mixtures, wherein the aforesaid modified starch has an average molecular weight (weight-average) from 50 to 2500 kDa and a propylene oxide content from 2.0 to 12.0 wt % (based on the weight of the starch modified by means of propylene oxide).

H): A cosmetic agent for coloring keratinic fibers, in particular human hair, including in a cosmetic carrier at least one oxidizing agent and at least one starch, modified by means of propylene oxide, selected from tapioca starch, potato starch, corn starch, or mixtures, wherein the aforesaid modified starch has an average molecular weight (weight-average) from 700 to 1000 kDa and a propylene oxide content from 2.0 to 12.0 wt % (based on the weight of the starch modified by means of propylene oxide).

I): A cosmetic agent for coloring keratinic fibers, in particular human hair, including in a cosmetic carrier at least one oxidizing agent and at least one starch, modified by means of propylene oxide, selected from tapioca starch, potato starch, corn starch, or mixtures, wherein the aforesaid modified starch has an average molecular weight (weight-average) from 50 to 2500 kDa, a propylene oxide content from 2.0 to 12.0 wt % (based on the weight of the starch modified by means of propylene oxide), and a viscosity from 3000 to 200,000 mPas (in 43-wt % aqueous solution, Brookfield viscometer, spindle 7, at 20° C. and 20 rpm).

J): A cosmetic agent for coloring keratinic fibers, in particular human hair, including in a cosmetic carrier at least one oxidizing agent and at least one starch, modified by means of propylene oxide, selected from tapioca starch, potato starch, corn starch, or mixtures, wherein the aforesaid modified starch has an average molecular weight (weight-average) from 50 to 2500 kDa, a propylene oxide content from 2.0 to 12.0 wt % (based on the weight of the starch modified by means of propylene oxide), and a viscosity from 1000 to 100,000 mPas (in 43-wt % aqueous solution, Brookfield viscometer, spindle 7, at 20° C. and 20 rpm).

K): A cosmetic agent for coloring keratinic fibers, in particular human hair, including in a cosmetic carrier at least one oxidizing agent and at least one starch, modified by means of propylene oxide, selected from tapioca starch, potato starch, corn starch, or mixtures, wherein the aforesaid modified starch has an average molecular weight (weight-average) from 700 to 1000 kDa, a propylene oxide content from 2.0 to 12.0 wt % (based on the weight of the starch modified by means of propylene oxide), and a viscosity from 3000 to 200,000 mPas (in 43-wt % aqueous solution, Brookfield viscometer, spindle 7, at 20° C. and 20 rpm).

L): A cosmetic agent for coloring keratinic fibers, in particular human hair, including in a cosmetic carrier at least one oxidizing agent and at least one starch, modified by means of propylene oxide, selected from tapioca starch, potato starch, corn starch, or mixtures, wherein the aforesaid modified starch has an average molecular weight (weight-average) from 700 to 1000 kDa, a propylene oxide content from 2.0 to 12.0 wt % (based on the weight of the starch modified by means of propylene oxide), and a viscosity from 10,000 to 100,000 mPas (in 43-wt % aqueous solution, Brookfield viscometer, spindle 7, at 20° C. and 20 rpm).

M): A cosmetic agent for coloring keratinic fibers, in particular human hair, including in a cosmetic carrier at least one oxidizing agent and at least one uncrosslinked tapioca starch, modified by means of propylene oxide, that has an average molecular weight (weight-average) from 50 to 2500 kDa and a propylene oxide content from 2.0 to 12.0 wt % (based on the weight of the tapioca starch modified by means of propylene oxide).

N): A cosmetic agent for coloring keratinic fibers, in particular human hair, including in a cosmetic carrier at least one oxidizing agent and at least one tapioca starch, modified by means of propylene oxide, that has an average molecular weight (weight-average) from 700 to 1000 kDa and a propylene oxide content from 2.0 to 12.0 wt % (based on the weight of the tapioca starch modified by means of propylene oxide).

O): A cosmetic agent for coloring keratinic fibers, in particular human hair, including in a cosmetic carrier at least one oxidizing agent and at least one tapioca starch, modified by means of propylene oxide, that has an average molecular weight (weight-average) from 50 to 2500 kDa, a propylene oxide content from 2.0 to 12.0 wt % (based on the weight of the tapioca starch modified by means of propylene oxide), and a viscosity from 3000 to 200,000 mPas (in 43-wt % aqueous solution, Brookfield viscometer, spindle 7, at 20° C. and 20 rpm).

P): A cosmetic agent for coloring keratinic fibers, in particular human hair, including in a cosmetic carrier at least one oxidizing agent and at least one tapioca starch, modified by means of propylene oxide, that has an average molecular weight (weight-average) from 50 to 2500 kDa, a propylene oxide content from 2.0 to 12.0 wt % (based on the weight of the tapioca starch modified by means of propylene oxide), and a viscosity from 1000 to 100,000 mPas (in 43-wt % aqueous solution, Brookfield viscometer, spindle 7, at 20° C. and 20 rpm).

Q): A cosmetic agent for coloring keratinic fibers, in particular human hair, including in a cosmetic carrier at least one oxidizing agent and at least one tapioca starch, modified by means of propylene oxide, that has an average molecular weight (weight-average) from 700 to 1000 kDa, a propylene oxide content from 2.0 to 12.0 wt % (based on the weight of the tapioca starch modified by means of propylene oxide), and a viscosity from 3000 to 200,000 mPas (in 43-wt % aqueous solution, Brookfield viscometer, spindle 7, at 20° C. and 20 rpm).

R): A cosmetic agent for coloring keratinic fibers, in particular human hair, including in a cosmetic carrier at least one oxidizing agent and at least one tapioca starch, modified by means of propylene oxide, that has an average molecular weight (weight-average) from 700 to 1000 kDa, a propylene oxide content from 2.0 to 12.0 wt % (based on the weight of the tapioca starch modified by means of propylene oxide), and a viscosity from 10,000 to 100,000 mPas (in 43-wt % aqueous solution, Brookfield viscometer, spindle 7, at 20° C. and 20 rpm).

The examples A) to R) of the cosmetic agent according to the present specification preferably include hydrogen peroxide and/or at least one addition product thereof as an oxidizing agent.

The cosmetic agents according to the present specification (preferably the cosmetic agents of embodiments A) to R)) include the aforesaid starches modified by means of propylene oxide preferably in a quantity from 0.01 wt % to 20 wt %, particularly preferably from 0.01 wt % to 10.0 wt %, very particularly preferably from 0.1 wt % to 5 wt %, most preferably from 0.1 to 2.0 wt %, based in each case on the weight of the ready-to-use agent.

It is preferred according to the present specification to use the agent according to the present specification in the context of a change in the color of the hair. For this purpose, the cosmetic agents additionally include at least one color-changing component.

The color-imparting compounds for purposes of the present specification are preferably selected from 1) at least one oxidation dye precursor of the developer component type and optionally additionally at least one coupler component; 2) at least one substantive dye; and/or 3) at least one precursor of bioanalogous dyes.

Particularly preferred color-imparting compounds are selected from at least one oxidation dye precursor of the developer component type and optionally additionally at least one coupler component.

Primary aromatic amines having a further free or substituted hydroxy or amino group located in the para- or ortho-position, diaminopyridine derivatives, heterocyclic hydrazones, 4-aminopyrazole derivatives, and 2,4,5,6-tetraminopyrimidine and derivatives thereof, are usually used as developer components.

It may be preferred according to the present specification to use, as a developer component, a p-phenylenediamine derivative or one of the physiologically acceptable salts thereof. Particularly preferred are p-phenylenediamine derivatives of formula (Ent1).

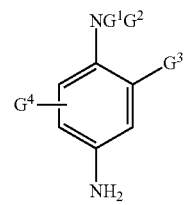

(Ent1)

In formula (Ent1):
G$^1$ denotes a hydrogen atom, a C$_1$ to C$_4$ alkyl residue, a C$_1$ to C$_4$ monohydroxyalkyl residue, a C$_2$ to C$_4$ polyhydroxyalkyl residue, a (C$_1$ to C$_4$) alkoxy-(C$_1$ to C$_4$) alkyl residue, a 4'-aminophenyl residue, or a C$_1$ to C$_4$ alkyl residue that is substituted with a nitrogen-containing group, with a phenyl residue, or with a 4'-aminophenyl residue,
G$^2$ denotes a hydrogen atom, a C$_1$ to C$_4$ alkyl residue, C$_1$ to C$_4$ monohydroxyalkyl residue, a C$_2$ to C$_4$ polyhydroxyalkyl residue, a (C$_1$ to C$_4$) alkoxy-(C$_1$ to C$_4$) alkyl residue, or a C$_1$ to C$_4$ alkyl residue that is substituted with a nitrogen-containing group,
G$^3$ denotes a hydrogen atom, a halogen atom such as a chlorine, bromine, iodine, or fluorine atom, a C$_1$ to C$_4$ alkyl residue, a C$_1$ to C$_4$ monohydroxyalkyl residue, a C$_2$ to C$_4$ polyhydroxyalkyl residue, a C$_1$ to C$_4$ hydroxyalkoxy residue, a C$_1$ to C$_4$ acetylaminoalkoxy residue, a C$_1$ to C$_4$ mesylaminoalkoxy residue, or a C$_1$ to C$_4$ carbamoylaminoalkoxy residue,
G$^4$ denotes a hydrogen atom, a halogen atom, or a C$_1$ to C$_4$ alkyl residue, or
if G$^3$ are G$^4$ are in the ortho-position with respect to one another, they can together form a bridging α,ω-alkylenedioxo group, for example an ethylenedioxy group.

Examples of the C$_1$ to C$_4$ alkyl residues recited as substituents in the compounds according to the present specification are the methyl, ethyl, propyl, isopropyl and butyl groups. Ethyl and methyl are preferred alkyl residues. C$_1$ to C$_4$ alkoxy residues preferred according to the present specification are, for example, a methoxy or an ethoxy group. A hydroxymethyl, 2-hydroxyethyl, 3-hydroxypropyl, or 4-hydroxybutyl group may also be recited as preferred examples of a $C_1$ to $C_4$ hydroxyalkyl group. A 2-hydroxyethyl group is particularly preferred. A particularly preferred $C_2$ to $C_4$ polyhydroxyalkyl group is the 1,2-dihydroxyethyl group. Examples of halogen atoms are, according to the present specification, F, Cl, or Br atoms; Cl atoms are very particularly preferred. The additional terms used are derived, according to the present specification, from the definitions given here. Examples of nitrogen-including groups of formula (Ent1) are, in particular, the amino groups, $C_1$ to $C_4$ monoalkylamino groups, $C_1$ to $C_4$ dialkylamino groups, $C_1$ to $C_4$ trialkylammonium groups, $C_1$ to $C_4$ monohydroxyalkylamino groups, imidazolinium, and ammonium.

Particularly preferred p-phenylenediamines of formula (Ent1) are selected from p-phenylenediamine, p-toluoylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis-(β-hydroxyethyl)-p-phenylenediamine, 4-N,N-bis-(β-hydroxyethyl)amino-2-methylaniline, 4-N,N-bis-(β-hydroxyethyl)amino-2-chloroaniline, 2-(β-hydroxyethyl)-p-phenylenediamine, 2-(α,β-dihydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl, □β-hydroxyethyl)-p-phenylenediamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-(β-acetylaminoethyloxy)-p-phenylenediamine, N-(β-methoxyethyl)-p-phenylenediamine, and 5,8-diaminobenzo-1,4-dioxane, as well as physiologically acceptable salts thereof.

p-Phenylenediamine derivatives of formula (Ent1) that are very particularly preferred according to the present specification are p-phenylenediamine, p-toluoylenediamine, 2-(β-hydroxyethyl)-p-phenylenediamine, 2-(α,β-dihydroxyethyl)-p-phenylenediamine, and N,N-bis-(β-hydroxyethyl)-p-phenylenediamine.

It can furthermore be preferred according to the present specification to use, as developer components, compounds that include at least two aromatic nuclei that are substituted with amino and/or hydroxyl groups.

Among the binuclear developer components that can be used in the agents in accordance with the specification may be cited, in particular, those compounds which correspond to formula (Ent2) below, as well as physiologically acceptable salts thereof.

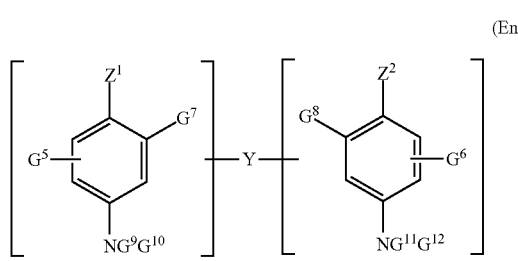

(Ent2)

In formula (Ent2):
$Z^1$ and $Z^2$ mutually independently denote a hydroxyl residue or $NH_2$ residue that is optionally substituted with a $C_1$ to $C_4$ alkyl residue, with a $C_1$ to $C_4$ hydroxyalkyl residue, and/or with a bridge Y, or that optionally is part of a bridging ring system, the bridge Y denotes an alkylene group having 1 to 14 carbon atoms, for example a linear or branched alkylene chain or an alkylene ring, which can be interrupted or terminated by one or more nitrogen-containing groups and/or by one or more heteroatoms such as oxygen, sulfur, or nitrogen atoms, and possibly can be substituted with one or more hydroxyl residues or $C_1$ to $C_8$ alkoxy residues, or a direct bond $G^5$ and $G^6$ mutually independently denote a hydrogen or halogen atom, a $C_1$ to $C_4$ alkyl residue, a $C_1$ to $C_4$ monohydroxyalkyl residue, a $C_2$ to $C_4$ polyhydroxyalkyl residue, a $C_1$ to $C_4$ aminoalkyl residue, or a direct bond to the bridge Y, $G^7$, $G^8$, $G^9$, $G^{10}$, $G^{11}$ and $G^{12}$ mutually independently denote a hydrogen atom, a direct bond to the bridge Y, or a $C_1$ to $C_4$ alkyl residue, In formula (Ent2), the compounds include only one bridge Y per molecule, and the compounds include at least one amino group that carries at least one hydrogen atom. The substituents used in formula (Ent2) are defined according to the present specification analogously to the statements made above.

Preferred binuclear developer components of formula (Ent2) are, in particular: N,N'-bis-(β-hydroxyethyl)-N,N'-bis-(4'-aminophenyl)-1,3-diaminopropan-2-ol, N,N'-bis-(β-hydroxyethyl)-N,N'-bis-(4'-aminophenyl)ethylenediamine, N,N'-bis-(4-aminophenyl)tetramethylenediamine, N,N'-bis-(β-hydroxyethyl)-N,N'-bis-(4-aminophenyl)tetramethylenediamine, N,N'-bis-(4-methylaminophenyl)tetramethylenediamine, N,N'-diethyl-N,N'-bis-(4'-amino-3'-methylphenyl)ethylenediamine, bis-(2-hydroxy-5-aminophenyl)methane, 1,3-bis-(2,5-diaminophenoxy)propan-2-ol, N,N'-bis-(4'-aminophenyl)-1,4-diazacycloheptane, N,N'-bis-(2-hydroxy-5-aminobenzyl)piperazine, N-(4'-aminophenyl)-p-phenylenediamine, and 1,10-bis-(2',5'-diaminophenyl)-1,4,7,10-tetraoxadecane, and physiologically acceptable salts thereof.

Very particularly preferred binuclear developer components of formula (Ent2) are N,N'-bis-(β-hydroxyethyl)-N,N'-bis-(4'-aminophenyl)-1,3-diaminopropan-2-ol, bis-(2-hydroxy-5-aminophenyl)methane, 1,3-bis-(2,5-diaminophenoxy)propan-2-ol, N,N'-bis-(4'-aminophenyl)-1,4-diazacycloheptane, and 1,10-bis-(2',5'-diaminophenyl)-1,4,7,10-tetraoxadecane, or a physiologically acceptable salt thereof.

It can furthermore be preferred according to the present specification to use as a developer component a p-aminophenol derivative or one of its physiologically acceptable salts. p-Aminophenol derivatives of formula (Ent3) are particularly preferred.

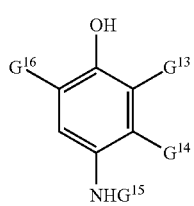

(Ent3)

In formula (Ent3):
$G^{13}$ denotes a hydrogen atom, a halogen atom, a $C_1$ to $C_4$ alkyl residue, a $C_1$ to $C_4$ monohydroxyalkyl residue, a $C_2$ to $C_4$ polyhydroxyalkyl residue, a $(C_1$ to $C_4)$ alkoxy-$(C_1$ to $C_4)$ alkyl residue, a $C_1$ to $C_4$ aminoalkyl residue, a hydroxy-$(C_1$ to $C_4)$ alkylamino residue, a $C_1$ to $C_4$ hydroxyalkoxy residue, a $C_1$ to $C_4$ hydroxyalkyl-($C_1$ to $C_4$) aminoalkyl residue, or a (di-$C_1$ to $C_4$ alkylamino)-($C_1$ to $C_4$) alkyl residue, and $G^{14}$ denotes a hydrogen or halogen atom, a $C_1$ to $C_4$ alkyl residue, a $C_1$ to $C_4$ monohydroxyalkyl residue, a $C_2$ to $C_4$ polyhydroxyalkyl residue, a ($C_1$ to $C_4$) alkoxy-($C_1$ to $C_4$) alkyl residue, a $C_1$ to $C_4$ aminoalkyl residue, or a $C_1$ to $C_4$ cyanoalkyl residue, $G^{15}$ denotes hydrogen, a $C_1$ to $C_4$ alkyl residue, a $C_1$ to $C_4$ monohydroxyalkyl residue, a $C_2$ to $C_4$ polyhydroxyalkyl residue, a phenyl residue, or a benzyl residue, and $G^{16}$ denotes notes hydrogen or a halogen atom.

The substituents used in formula (Ent3) are defined according to the present specification analogously to the statements made above.

Preferred p-aminophenols of formula (Ent3) are, in particular, p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(β-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-(α,β-dihydroxyethyl)phenol, 4-amino-2-fluorophenol, 4-amino-2-chlorophenol, 4-amino-2,6-dichlorophenol, 4-amino-2-(diethylaminomethyl)phenol, and physiologically acceptable salts thereof.

Very particularly preferred compounds of formula (Ent3) are p-aminophenol, 4-amino-3-methylphenol, 4-amino-2-aminomethylphenol, 4-amino-2-(α,β-dihydroxyethyl)phenol, and 4-amino-2-(diethylaminomethyl)phenol.

The developer component can furthermore be selected from o-aminophenol and derivatives thereof, for example 2-amino-4-methylphenol, 2-amino-5-methylphenol, or 2-amino-4-chlorophenol.

The developer component can moreover be selected from heterocyclic developer components, for example pyridine derivatives, pyrimidine derivatives, pyrazole derivatives, pyrazolopyrimidine derivatives and physiologically acceptable salts thereof.

Preferred pyridine derivatives are in particular the compounds that are described in British patents GB 1 026 978 and GB 1 153 196, such as 2,5-diaminopyridine, 2-(4'-methoxyphenyl)amino-3-aminopyridine, 2,3-diamino-6-methoxypyridine, 2-(β-methoxyethyl)amino-3-amino-6-methoxypyridine, and 3,4-diaminopyridine.

Preferred pyrimidine derivatives are in particular the compounds described in German patent DE 2 359 399, Japanese application JP 02019576 A2, or German application WO 96/15765, such as 2,4,5,6-tetraminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine, and 2,5,6-triaminopyrimidine.

Preferred pyrazole derivatives are in particular the compounds described in German patents DE 3 843 892, DE 4 133 957, and patent applications WO 94/08969, WO 94/08970, EP-740 931, and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, and 3,5-diamino-4-(β-hydroxyethyl)amino-1-methylpyrazole.

The coupler components generally used are m-phenylenediamine derivatives, naphthols, resorcinol and resorcinol derivatives, pyrazolones, and m-aminophenol derivatives, as well as heterocyclic compounds.

Coupler components preferred according to the present specification are:

m-aminophenol and derivatives thereof, for example 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluororacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol, and 2,4-dichloro-3-aminophenol, o-aminophenol and derivatives thereof, m-diaminobenzene and derivatives thereof, for example 2,4-diaminophenoxyethanol, 1,3-bis-(2',4'-diaminophenoxy)propane, 1-methoxy-2-amino-4-(2'-hydroxyethylamino)benzene, 1,3-bis-(2'4'-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, and 1-amino-3-bis-(2'-hydroxyethyl)aminobenzene, o-diaminobenzene and derivatives thereof, for example 3,4-diaminobenzoic acid and 2,3-diamino-1-methylbenzene, di- or trihydroxybenzene derivatives, for example resorcinol, resorcinol monomethyl ether, 2-methylresorcinol, 5-methylresorcinol, 2,5-dimethylresorcinol, 2-chlororesorcinol, 4-chlororesorcinol, pyrogallol, and 1,2,4-trihydroxybenzene, pyridine derivatives, for example 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, and 3,5-diamino-2,6-dimethoxypyridine, naphthalene derivatives, for example 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxynaphthalene, 1,8-dihydroxynaphthalene, 2,7-dihydroxynaphthalene, and 2,3-dihydroxynaphthalene, morpholine derivatives, for example 6-hydroxybenzomorpholine and 6-aminobenzomorpholine, quinoxaline derivatives, for example 6-methyl-1,2,3,4-tetrahydroquinoxaline, pyrazole derivatives, for example 1-phenyl-3-methylpyrazol-5-one, indole derivatives, for example 4-hydroxyindole, 6-hydroxyindole, and 7-hydroxyindole, pyrimidine derivatives, for example 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine, and 4,6-dihydroxy-2-methylpyrimidine, or methylenedioxybenzene derivatives, for example 1-hydroxy-3,4-methylenedioxybenzene, 1-amino-3,4-methylenedioxybenzene, and 1-(2'-hydroxyethyl)amino-3,4-methylenedioxybenzene, as well as physiologically acceptable salts thereof.

Coupler components particularly preferred according to the present specification are 1-naphthol, 1,5- and 2,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol, and 2,6-dihydroxy-3,4-dimethylpyridine, and physiologically acceptable salts of the aforesaid compounds.

The cosmetic agents according to the present specification include the developer components preferably in a quantity from 0.005 to 10.0 wt %, preferably from 0.1 to 5.0 wt %, based in each case on the total agent.

The cosmetic agents according to the present specification include the coupler components preferably in a quantity from 0.005 to 10.0 wt %, preferably from 0.1 to 5.0 wt %, based in each case on the total agent.

It is preferred to use, as precursors of bioanalogous dyes, those indoles and indolines which include at least one hydroxy group or amino group, preferably as a substituent on the six-membered ring. These groups can carry further substituents, for example in the form of an etherification or esterification of the hydroxy group, or an alkylation of the amino group. In a second preferred example, the coloring agents include at least one indole derivative and/or indoline derivative.

Particularly suitable as precursors of bioanalogous hair dyes are derivatives of 5,6-dihydroxyindoline of formula (IVa):

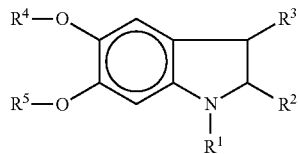

(IVa)

in which, mutually independently, $R^1$ denotes hydrogen, a $C_1$ to $C_4$ alkyl group, or a $C_1$ to $C_4$ hydroxyalkyl group, $R^2$ denotes hydrogen or a —COOH group, wherein the —COOH group can also be present as a salt with a physiologically acceptable cation, $R^3$ denotes hydrogen or a $C_1$ to $C_4$ alkyl group, $R^4$ denotes hydrogen, a $C_1$ to $C_4$ alkyl group, or a —CO—$R^6$ group in which $R^6$ denotes a $C_1$ to $C_4$ alkyl group, and $R^5$ denotes one of the groups recited under $R^4$, as well as physiologically acceptable salts of these compounds with an organic or inorganic acid.

Particularly preferred derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, and 6-hydroxyindoline, 6-aminoindoline, and 4-aminoindoline.

Particularly to be emphasized within this group are N-methyl-5,6-dihydroxyindoline, N-ethyl-5,6-dihydroxyindoline, N-propyl-5,6-dihydroxyindoline, N-butyl-5,6-dihydroxyindoline, and in particular 5,6-dihydroxyindoline.

Also outstandingly suitable as precursors of bioanalogous hair dyes are derivatives of 5,6-dihydroxyindole of formula (IVb):

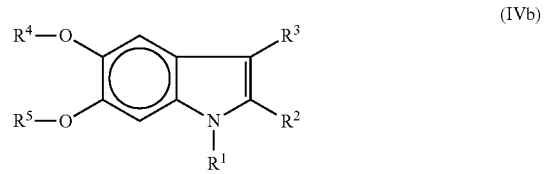

(IVb)

in which, mutually independently, $R^1$ denotes hydrogen, a $C_1$ to $C_4$ alkyl group, or a $C_1$ to $C_4$ hydroxyalkyl group, $R^2$ denotes hydrogen or a —COOH group, where the —COOH group can also be present as a salt with a physiologically acceptable cation, $R^3$ denotes hydrogen or a $C_1$ to $C_4$ alkyl group, $R^4$ denotes hydrogen, a $C_1$ to $C_4$ alkyl group, or a —CO—$R^6$ group in which $R^6$ denotes a $C_1$ to $C_4$ alkyl group, and $R^5$ denotes one of the groups recited under $R^4$, as well as physiologically acceptable salts of these compounds with an organic or inorganic acid.

Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole, and 4-aminoindole.

To be emphasized within this group are N-methyl-5,6-dihydroxyindole, N-ethyl-5,6-dihydroxyindole, N-propyl-5,6-dihydroxyindole, N-butyl-5,6-dihydroxyindole, and in particular 5,6-dihydroxyindole.

Preferred substantive dyes that are utilized in the cosmetic agents as a color-changing component are nitrophenylenediamines, nitroaminophenols, azo dyes, anthraquinones, or indophenols. Preferred substantive dyes are the compounds known by the international designations or commercial names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, as well as 1,4-diamino-2-nitrobenzene, 2-amino-4-nitrophenol, 1,4-bis-(β-hydroxyethyl)amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-1-hydroxy-4-nitrobenzene.

The cosmetic agents can furthermore include a cationic substantive dye. Particularly preferred in this context are:

(a) cationic triphenylmethane dyes, for example Basic Blue 7, Basic Blue 26, Basic Violet 2, and Basic Violet 14, (b) aromatic systems that are substituted with a quaternary nitrogen group, for example Basic Yellow 57, Basic Red 76, Basic Blue 99, Basic Brown 16, and Basic Brown 17, and (c) substantive dyes that include a heterocycle which comprises at least one quaternary nitrogen atom, as recited for example in EP-A2-998 908, to which reference is explicitly made here, in claims 6 to 11.

Preferred cationic substantive dyes of group (c) are in particular the following compounds:

(DZ1)
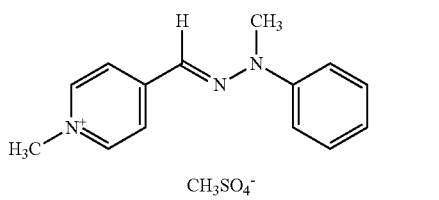

(DZ2)
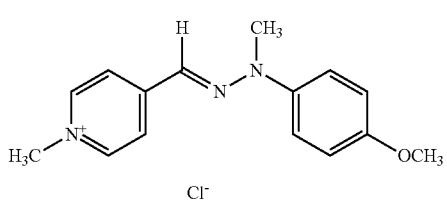

(DZ3)
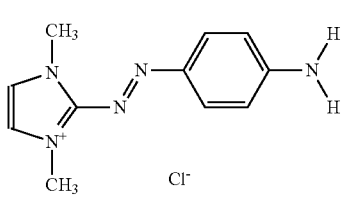

(DZ4)
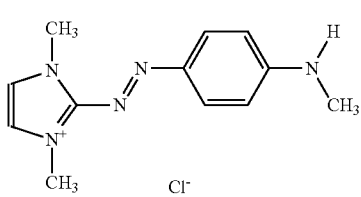

(DZ5)
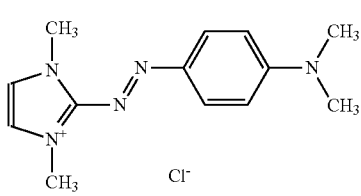

(DZ6)
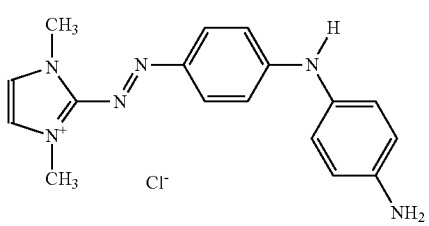

(DZ7)
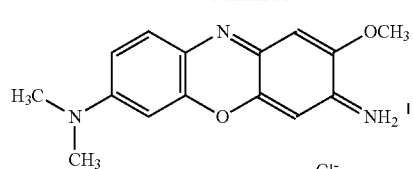

(DZ8)
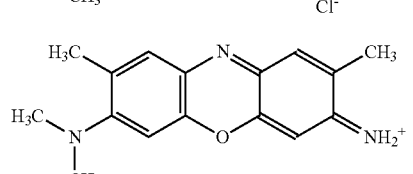

(DZ9)
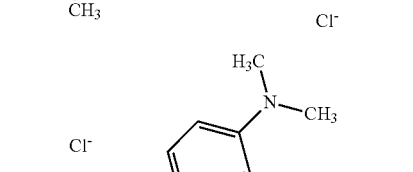

The compounds of formulas (DZ1), (DZ3), and (DZ5), which are also known by the names Basic Yellow 87, Basic Orange 31, and Basic Red 51, are very particularly preferred cationic substantive dyes of group (c).

The cationic substantive dyes that are marketed under the trade name ARIANOR®. ARIANOR® is a dye manufactured by Sensient (Goldmann) are likewise very particularly preferred cationic substantive dyes according to the present specification.

The cosmetic agents include the substantive dyes preferably in a quantity from 0.01 to 20.0 wt %, based on the ready-to-use agent.

The cosmetic agents according to the present specification may furthermore also include naturally occurring dyes, such as those included e.g. in red henna, neutral henna, black henna, chamomile blossoms, sandalwood, black tea, buckthorn bark, salvia, logwood, madder root, catechu, Spanish cedar, and alkanna root.

When the dye precursors and the oxidizing agent are stored separately, the actual oxidative coloring agent is produced immediately before use, by mixing. In a preferred example, the cosmetic agent is therefore mixed, before application, from one composition including in a cosmetic carrier at least one color-changing component and a further composition including in a cosmetic carrier at least one oxidizing agent.

When oxidizing agents are used, the ready-to-use preparation is usefully produced immediately before use by mixing a composition including the oxidizing agent with the composition including the color-changing component. The resulting ready-to-use hair preparation should preferably have a pH in the range from 6 to 12, in particular from pH 7.5 to 10.

In a further preferred example of the present specification, the effect can be further optimized by adding at least one fatty substance. As used in the present specification and in the appended claims, the term "fatty substances" refer to fatty acids, fatty alcohols, natural and synthetic waxes, which can be present both in solid form and in liquid form in aqueous dispersion, and natural and synthetic cosmetic oil components. Cosmetic agents of this example are present preferably as an oil-in-water emulsion, water-in-oil emulsion, or dispersion.

Fatty acids that can be used are linear and/or branched, saturated and/or unsaturated fatty acids having 6 to 30 carbon atoms. Fatty acids having 10 to 22 carbon atoms are preferred. Among those that might be recited are, for example, isostearic acids, such as the commercial products EMERSOL® 871 and EMERSOL® 875, and isopalmitic acids such as the commercial product EDENOR® IP 95, as well as all further fatty acids marketed under the EDENOR® commercial designations. Further typical examples of such fatty acids are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselinic acid, linoleic acid, linolenic acid, eleostearic acid, arachidic acid, gadoleic acid, behenic acid, and erucic acid, as well as industrial mixtures thereof that occur, for example, upon high-pressure cleavage of natural fats and oils, upon oxidation of aldehydes from Roelen oxosynthesis, or upon dimerization of unsaturated fatty acids. The fatty acid cuts that are obtainable from coconut oil or palm oil are usually particularly preferred; the use of stearic acid is particularly preferred.

The quantity used is 0.1 to 15.0 wt % based on the total agent. In a preferred example the quantity is 0.5 to 10.0 wt %, and quantities from 1 to 5 wt % are very particularly advantageous.

Fatty alcohols that can be used are saturated, mono- or polyunsaturated, branched or unbranched fatty alcohols having $C_6$ to $C_{30}$, preferably $C_{10}$ to $C_{22}$, and very particularly preferably $C_{12}$ to $C_{22}$ carbon atoms. Usable in the context of the specification are, for example, decanol, octanol, octenol, dodecenol, decenol, octadienol, dodecadienol, decadienol, oleyl alcohol, erucyl alcohol, ricinol alcohol, stearyl alcohol, isostearyl alcohol, cetyl alcohol, lauryl alcohol, myristyl alcohol, arachidyl alcohol, capryl alcohol, caprinyl alcohol, linoleyl alcohol, linolenyl alcohol, and behenyl alcohol, as well as Guerbet alcohols thereof, this listing being intended to be exemplary and not limiting in nature. The fatty alcohols derive, however, from preferably natural fatty acids; it is usually possible to proceed from an extraction from the esters of the fatty acids by reduction. Also usable according to the present specification are those fatty alcohol cuts which are generated by the reduction of naturally occurring triglycerides such as beef tallow, palm oil, peanut oil, colza oil, cottonseed oil, soy oil, sunflower oil, and linseed oil, or from fatty acid esters resulting from transesterification products thereof with corresponding alcohols, and thus represent a mixture of different fatty alcohols. Such substances are available commercially, for example, under the designations STENOL® fatty alcohol, e.g. STENOL® 1618 fatty alcohol, or LANETTE® fatty alcohols, e.g. LANETTE® 0 fatty alcohol, or LOROL® fatty alcohol, e.g. LOROL® C8 fatty alcohol, LOROL® C14 fatty alcohol, LOROL® C18 fatty alcohol, LOROL® C8-18 fatty alcohol, HD-OCENOL® fatty alcohol, CRODACOL® fatty alcohol, e.g. CRODACOL® CS fatty alcohol, NOVOL® fatty alcohol, EUTANOL® G fatty alcohol, GUERBITOL® 16 fatty alcohol, GUERBITOL® 18 fatty alcohol, GUERBITOL® 20 fatty alcohol, ISOFOL® 12 fatty alcohol, ISOFOL® 16 fatty alcohol, ISOFOL® 24 fatty alcohol, ISOFOL® 36 fatty alcohol, ISOCARB® 12 fatty alcohol, ISOCARB® 16 fatty alcohol, or ISOCARB® 24 fatty alcohol. It is of course also possible according to the present specification to use wool-wax alcohols such as those available commercially under the designations CORONA® lanolin, WHITE SWAN® lanolin, CORONET® wool-wax alcohol, or FLUILAN® wool-wax alcohol. The fatty alcohols are employed in quantities from 0.1 to 20.0 wt % based on the total preparation, preferably in quantities from 0.1 to 10.0 wt %.

Natural or synthetic waxes that can be used according to the present specification are solid paraffins or isoparaffins, carnauba waxes, beeswaxes, candelilla waxes, ozocerites, ceresin, spermaceti, sunflower wax, fruit waxes such as apple wax or citrus wax, microcrystalline waxes made from PE or PP. Such waxes are obtainable, for example, via Kahl & Co., Trittau.

Among the natural and synthetic cosmetic oily substances that can enhance the effect of the active agent according to the present specification may be listed, for example:

Vegetable oils. Examples of such oils are sunflower oil, olive oil, soy oil, rapeseed oil, almond oil, jojoba oil, orange oil, wheat germ oil, peach-kernel oil, and the liquid components of coconut oil. Also suitable, however, are other triglyceride oils such as the liquid components of beef tallow, as well as synthetic triglyceride oils.

Liquid paraffin oils, isoparaffin oils, and synthetic hydrocarbons, as well as di-n-alkyl ethers having a total of between 12 and 36 carbon atoms, in particular 12 to 24 carbon atoms, for example di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether, and n-hexyl-n-undecyl ether, as well as ditert-butyl ether, diisopentyl ether, di-3-ethyldecyl ether, tert-butyl-n-octyl ether, isopentyl-n-octyl ether, and 2-methylpentyl-n-octyl ether. The compounds 1,3-di-(2-ethylhexyl)cyclohexane (CETIOL® S) and di-n-octyl ether (CETIOL® OE), available as commercial products, can be preferred.

Ester oils. "Ester oils" are to be understood as the esters of $C_6$ to $C_{30}$ fatty acids with $C_2$ to $C_{30}$ fatty alcohols. The monoesters of fatty acids with alcohols having 2 to 24 carbon atoms are preferred. Examples of fatty acid components employed in the esters are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselinic acid, linoleic acid, linolenic acid, eleostearic acid, arachidic acid, gadoleic acid, behenic acid, and erucic acid, as well as industrial mixtures thereof that occur, for example, upon high-pressure cleavage of natural fats and oils, upon oxidation of aldehydes from Roelen oxosynthesis, or upon dimerization of unsaturated fatty acids. Examples of the fatty alcohol components in the ester oils are isopropyl alcohol, hexanol, octanol, 2-ethylhexyl alcohol, decanol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, eleostearyl alcohol, arachyl alcohol, gadoleyl alcohol, behenyl alcohol, erucyl alcohol, and brassidyl alcohol, as well as industrial mixtures thereof that occur, for example, upon high-pressure hydrogenation of industrial methyl esters based on fats and oils or aldehydes from Roelen oxosynthesis, and as a monomer fraction upon dimerization of unsaturated fatty alcohols. Particularly preferred according to the present specification are isopropyl myristate (RILANIT® IPM), isononanoic acid C16-18 alkyl ester (CETIOL® SN a hydrocarbon), 2-ethylhexyl palmitate (CEGESOFT® 24), stearic acid 2-ethylhexyl ester (CETIOL® 868 a hydrocarbon), cetyl oleate, glycerol tricaprylate, coconut fatty alcohol caprinate/caprylate (CETIOL® LC), n-butyl stearate, oleyl erucate (CETIOL® J 600), isopropyl palmitate (RILANIT® IPP), Oleyl Oleate (CETIOL®), lauric acid hexyl ester (CETIOL® A), di-n-butyl adipate (CETIOL® B), myristyl myristate (CETIOL® MM), Cetearyl Isononanoate (CETIOL® SN), oleic acid decyl ester (CETIOL® V).

Dicarboxylic acid esters such as di-n-butyl adipate, di(2-ethylhexyl)adipate, di(2-ethylhexyl) succinate, and diisotridecyl acelaate, as well as diol esters such as ethylene glycol dioleate, ethylene glycol diisotridecanoate, propylene glycol di(2-ethyl hexanoate), propylene glycol diisostearate, propylene glycol dipelargonate, butanediol diisostearate, neopentyl glycol dicaprylate.

Symmetrical, asymmetrical, or cyclic esters of carbonic acid with fatty alcohols, for example described in German Application DE 197 56 454, glycerol carbonate or dicaprylyl carbonate (CETIOL® CC).

Mono-, di-, and trifatty acid esters of saturated and/or unsaturated linear and/or branched fatty acids with glycerol, for example MONOMULS 90-O18, MONOMULS® 90-L12, or CUTINA® MD.

The quantity used is 0.1 to 50.0 wt % based on the total agent, preferably 0.1 to 20.0 wt %, and particularly preferably 0.1 to 15.0 wt % based on the total agent.

The total quantity of oily and fatty components in the agents according to the present specification is usually 6 to 45 wt %, based on the total agent. Quantities from 10 to 35 wt % are preferred according to the present specification.

The cosmetic agents according to the present specification can moreover include further active agents, adjuvants, and additives, for example nonionic polymers; cationic polymers; zwitterionic and amphoteric polymers; anionic polymers such as polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic acid anhydride copolymers, and acrylic acid/ethyl acrylate/N-tert-butylacrylamide terpolymers; hair-conditioning compounds such as phospholipids; protein hydrolysates, in particular hydrolysates of elastin, collagen, keratin, milk protein, soy protein, and wheat protein, condensation products thereof with fatty acids, and quaternized protein hydrolysates; perfume oils, dimethylisosorbide, and cyclodextrins; fiber-structure-improving active agents, in particular mono-, di- and oligosaccharides such as glucose, galactose, fructose, fruit sugars, and lactose; cationic surfactants; defoamers; antidandruff active substances; light protection agents, in particular derivatized benzophenones, cinnamic acid derivatives, and triazines; active agents such as allantoin, pyrrolidonecarboxylic acids and salts thereof, as well as bisabolol; vitamins, provitamins, and vitamin precursors, in particular those of groups A, $B_3$, $B_5$, $B_6$, C, E, F, and H; plant extracts, in particular the extracts from green tea, oak bark, stinging nettle, witch hazel, hops, henna, chamomile, burdock, horsetail, whitethorn, linden blossom, almond, aloe vera, pine needles, horse chestnut, sandalwood, juniper, coconut, mango, apricot, lemon, wheat, kiwi, melon, orange, grapefruit, sage, rosemary, birch, mallow, lady's smock, wild thyme, yarrow, thyme, melissa, restharrow, coltsfoot, hibiscus, meristem, ginseng, or ginger root; cholesterol; consistency agents; fats and waxes; complexing agents; swelling and penetration substances; opacifiers; luster agents; solid pigments; stabilizing agents for hydrogen peroxide and other oxidizing agents; propellants; antioxidants.

The preferred examples of the first subject of the specification apply mutatis mutandis regarding the second subject of the specification.

A third subject of the present specification is a method for oxidative hair treatment in which an oxidative cosmetic agent including in a cosmetic carrier at least one oxidizing agent is applied onto the hair and is rinsed out of the hair after a contact time. Also in the method:

immediately before application of the oxidative cosmetic agent, a cosmetic agent including in a cosmetic carrier at least one starch, modified by means of propylene oxide, that possesses an average molecular weight (weight-average) from 50 to 2500 kDa and a propylene oxide content from 0.1 to 20.0 wt % (based on the weight of the starch modified by means of propylene oxide), is applied and optionally is rinsed off again after a contact time, and/or the oxidative cosmetic agent additionally includes at least one starch, modified by means of propylene oxide, that possesses an average molecular weight (weight-average) from 50 to 2500 kDa and a propylene oxide content from 0.1 to 20.0 wt % (based on the weight of the starch modified by means of propylene oxide).

The contact time of the aforesaid starch modified by means of propylene oxide is preferably 1 to 100 minutes, particularly preferably 5 to 50 minutes.

It is in turn preferred according to the present specification to utilize the method according to the present specification in the context of an oxidative hair coloring process, oxidative hair bleaching, or retention in the context of a permanent wave. It is preferred here to utilize the aforesaid starch modified by means of propylene oxide on the hair together with the oxidizing agent.

In a preferred example of the method according to the present specification as an oxidative hair coloring method, the aforesaid starch modified by means of propylene oxide is preferably utilized, in one step, as a constituent of a cosmetic agent including, in a cosmetic carrier, additionally at least one oxidizing agent and at least one oxidation dye precursor.

In addition, in a further step of the method, in the context of a post-treatment an agent including, in a cosmetic carrier, at least one hair-conditioning compound in combination with at least one aforesaid starch modified by means of propylene oxide is formed and can optionally be used on the hair. Examples of these post-treatment agents can be gathered from the Examples section of this application.

The oxidative hair coloring agents of this example are preferably two-component agents. The first component includes, in a cosmetic carrier, at least one compound from the group that is constituted from at least one aforesaid starch modified by means of propylene oxide, and at least one oxidation dye precursor. The second component includes, in a cosmetic carrier, at least one oxidizing agent. These components are formulated separately from one another each in one compartment, and are furnished together in one packaging unit (kit). The two components are mixed with one another shortly before use.

In the example of the method according to the present specification as an oxidative hair bleaching method, the aforesaid starch modified by means of propylene oxide is preferably utilized in one step as a constituent of a cosmetic agent additionally including, in a cosmetic carrier, at least one oxidizing agent and at least one bleach intensifier.

The oxidative hair bleaching agents of this example are preferably two- or three-component agents. The first component includes, in a cosmetic carrier, at least one compound from the group that is constituted from at least one aforesaid starch modified by means of propylene oxide, and optionally at least one bleach intensifier, selected in particular from salts of peroxodisulfate. The bleach intensifier can also be formulated separately from the aforesaid starch modified by means of propylene oxide, for example in powder form, as an anhydrous paste or anhydrous oil. A three-component agent is thereby obtained. The last component includes, in a cosmetic carrier, at least one oxidizing agent. All the components are preferably formulated separately from one another each in one compartment, and are furnished together in one packaging unit (kit). All the components are mixed with one another shortly before use.

The multi-component agents described above for carrying out the method according to the present specification can be furnished in one packaging unit. The packaging unit either can comprise at least one container that contains the agent of the second subject of the specification, or can comprise at least two containers, wherein a first container contains an oxidative cosmetic agent including, in a cosmetic carrier, at least one oxidizing agent; a second container contains a cosmetic agent included in a cosmetic carrier; and optionally a third container contains at least one bleach intensifier embedded in a cosmetic carrier. All the containers can also be chambers of a multi-chamber receptacle.

The statements made for the first and the second subject of the specification apply mutatis mutandis regarding the third subject of the specification.

EXAMPLES 1.0 Oxidative Hair Treatment 1.0 wt % PGE-1 (a tapioca starch, modified with 5.5 wt % propylene oxide, having an average molecular weight ($M_W$) from 700 to 900 kDa and a viscosity of 55,000 mPas (43-wt % aqueous solution)) was incorporated into the color cream of the commercial product IGORA ROYAL® 6-88. The resulting modified color cream was mixed, immediately before application onto hair strands (1 g "European natural hair %" standardized hair, batch No. 06/2010, N93 of Kerling International, Germany, bonded at one end to produce a hair bundle), with a commercially usual 6-wt % hydrogen-peroxide-containing OXIGENTA® developer dispersion at a weight ratio of 1 to 1, to produce a hair coloring agent according to the present specification.

The ready-to-use coloring agent was then applied onto a hair strand at a weight ratio of 4 grams (g) coloring agent to 1 g hair, allowed to act for 30 minutes at 32° C., and rinsed off the fibers. A total of 12 hair strands were colored therewith. In addition, 12 hair strands were colored according to the above procedure using the above commercial product without addition of the aforesaid tapioca starch (not according to the specification).

2.0 Combing Work

The hair strands were moistened with water by spraying, and pre-combed three times by hand. The measurements were repeated before utilization of the oxidative hair treatment agents. The arithmetic mean was calculated in each case as a value for the combing work.

TABLE (1)

Table 1: Wet combing work

| | Combing work, before milliJoules (mJ) | Combing work, after (mJ) |
|---|---|---|
| Commercial product | 267 | 388 |
| Agent according to the present specification | 269 | 327 |

The data in Table (1) shows that use of the aforesaid starches in oxidative hair treatment agents reduces the increase in combing work brought about by the oxidative hair treatment.

3.0 Oxidative Hair Treatment Agents

The following formulas were made available using known manufacturing methods, using the commercial products below as raw materials:

HYDRENOL® D $C_{16}$-$C_{18}$ fatty alcohol (INCI name: Cetearyl Alcohol) (Cognis Deutschland)

LOROL® techn. $C_{12}$-$C_{18}$ fatty alcohol (INCI name: Coconut Alcohol) (Cognis Deutschland)

STENOL® 16/18 $C_{16-18}$ fatty alcohol (INCI name: Cetearyl Alcohol) (Cognis)

LOROL® 16 INCI name: Cetyl Alcohol (Cognis)

EUMULGIN® B1 Cetyl stearyl alcohol with 12 EO units (INCI name: Ceteareth-12) (Cognis Deutschland)

EUMULGIN® B2 Cetyl stearyl alcohol with approx. 20 EO units (INCI name: Ceteareth-20) (Cognis Deutschland)

EDENOR® C14 Myristic acid (INCI name: Myristic Acid) (Cognis)

TURPINAL® SL 1-hydroxyethane-1,1-diphosphonic acid (INCI name: Etidronic Acid, Aqua (Water)) (Solutia)

PLANTAPON® LGC Alkyl polyglucoside carboxylate sodium salt; 30% active substance (Cognis Deutschland)

TEXAPON® NSO UP Sodium lauryl ether sulfate (27% active substance; INCI: Sodium Laureth Sulfate) (manufacturer: COGNIS)

TEXAPON® K14S70C Lauryl myristyl ether sulfate sodium salt (approx. 68% to 73% active substance content; INCI name: Sodium Myreth Sulfate) (Cognis)

DISPONIL® FES 77 IS Fatty alcohol ether sulfate (approx. 31-33% active substance content in water; INCI name: Sodium Coceth-30 Sulfate) (Cognis)

AKYPO® Soft 45 NV 2-($C_{12-14}$ fatty alcohol ethoxylate (4.5 EO)) acetic acid sodium salt; 21% active substance; INCI name: Sodium Laureth-5 Carboxylate (KAO)

GLUADIN® W 40 Wheat protein hydrolysate (min. 40% solids; INCI name: Aqua (Water), Hydrolyzed Wheat Protein, Sodium Benzoate, Phenoxyethanol, Methylparaben, Propylparaben) (Cognis)

PLANTACARE® 1200 UP $C_{12-16}$ fatty alcohol 1.4 glucoside (approx. 50-53% active substance content; INCI name: Lauryl Glucoside, Aqua (Water)) (Cognis)

LAMESOFT® PO 65 Alkyl polyglucoside/oleic acid monoglyceride mixture (approx. 65-70% solids; INCI name: Coco-Glucoside, Glyceryl Oleate, Aqua (Water)) (Cognis)

ACULYN® 33 30 wt % active substance in water (INCI name: Acrylates Copolymer) (Rohm & Haas)

DOW CORNING® DB 110 A Nonionogenic silicone emulsion (10 wt % active substance) (INCI name: Dimethicone) (Dow Corning)

ARISTOFLEX® AVC Copolymer of vinylpyrrolidone and ammonium acryloyldimethyl taurate; (INCI name: Ammonium Acryloyldimethyl Taurate/VP Copolymer, t-Butyl Alcohol) (Clariant)

POLYMER® W 37194 Approx. 20 wt % active substance content in water; INCI name: Acrylamidopropyltrimonium Chloride/Acrylates Copolymer (Stockhausen)

CREMOPHOR® A 25 $C_{16-18}$ fatty alcohol ethoxylated with 25 units of ethylene oxide (INCI name: Ceteareth-25) (BASF)

3.1 Hair-Bleaching Agents

The hair-bleaching agents B1, B2, and B3 are each made up of a hair-bleaching cream and an accompanying developer, as well as a bleach intensifier. In order to manufacture the ready-to-use hair-bleaching agent, 50 grams (g) of the bleach intensifier was added to 50 g of the corresponding hair-bleaching cream. 20 g of the corresponding developer was added while stirring. Upon application onto head hair and with a contact time of 30 minutes, outstanding lightening was observed after rinsing and drying. The hair was well-groomed, had a natural shine, and was easy to comb. All numbers in Tables (2) and (3) indicate a weight percent of a particular component.

TABLE (2)

Hair-Bleaching Agents
3.1.1 Hair-bleaching cream

|  | B1 | B2 | B3 |
|---|---|---|---|
| STENOL 1618 | 10.00 | 10.00 | 10.00 |
| LOROL techn. | 3.00 | 3.00 | 3.00 |
| EUMULGIN B2 | 3.00 | 3.00 | 3.00 |
| Ammonium sulfate | 1.00 | 1.00 | 1.00 |
| TURPINAL SL | 0.20 | 0.20 | 0.20 |
| GLUADIN W 40 | 4.00 | 4.00 | 4.00 |
| Ammonia, 25% | 0.62 | 0.62 | 0.62 |
| PGE-1 | 1.0 | 1.5 | 0.75 |
| Water | to 100 | to 100 | to 100 |

TABLE (3)

Developer
3.1.2 Developer

|  | B1 | B2 | B3 |
|---|---|---|---|
| LOROL techn. | 3.60 | 3.60 | 3.60 |
| EUMULGIN B2 | 0.90 | 0.90 | 0.90 |
| DISPONIL FES 77 IS | 2.25 | 2.25 | 2.25 |
| Hydrogen peroxide, 50% | 24.0 | 24.0 | 24.0 |
| TURPINAL SL | 1.50 | 1.50 | 1.50 |
| ACULYN 33A | 15.0 | 15.0 | 15.0 |
| Water | to 100 | to 100 | to 100 |

TABLE (4)

Bleach Intensifier
3.1.3 Bleach Intensifier

| $(NH_4)_2S_2O_8$ | 96 |
|---|---|
| AEROSIL ® 200 | 4 |

In Table (4), the values indicate a weight percent of the different components within the bleach intensifier.

3.2 Oxidative Coloring Agents

The coloring agents F1 to F16 are each made up of a color cream and an accompanying developer. In order to manufacture the ready-to-use coloring agent, 50 g of the color cream was added to 50 g of the corresponding hair-bleaching cream. Upon application onto head hair and with a contact time of 30 minutes, an outstanding color result was observed after rinsing and drying. The hair had a well-groomed external appearance and a natural shine, and was easy to comb. The values indicated in Tables (5) and (6) represent weight percentages of the components.

TABLE (5)

Coloring Agents
3.2.1 Color creams

|  | F1 | F2 | F3 | F4 | F5 | F6 | F7 | F8 |
|---|---|---|---|---|---|---|---|---|
| HYDRENOL D | 5.50 | 5.50 | 5.50 | 5.50 | 5.50 | 5.50 | 5.50 | 5.50 |
| LOROL 16 | 2.00 | 2.00 | 2.00 | 2.00 | 2.00 | 2.00 | 2.00 | 2.00 |
| EUMULGIN B1 | 0.50 | 0.50 | 0.50 | 0.50 | 0.50 | 0.50 | 0.50 | 0.50 |
| EUMULGIN B2 | 0.50 | 0.50 | 0.50 | 0.50 | 0.50 | 0.50 | 0.50 | 0.50 |
| LAMESOFT PO 65 | 2.00 | 2.00 | 2.00 | 2.00 | 2.00 | 2.00 | 2.00 | 2.00 |
| AKYPO Soft 45 NV | 10.00 | 10.00 | 10.00 | 10.00 | 10.00 | 10.00 | 10.00 | 10.00 |
| TEXAPON K 14 S, 70% | 2.80 | 2.80 | 2.80 | 2.80 | 2.80 | 2.80 | 2.80 | 2.80 |
| Ammonia, 25% | 6.50 | 6.50 | 6.50 | 6.50 | 6.50 | 6.50 | 6.50 | 6.50 |
| TURPINAL SL | 0.20 | 0.20 | 0.20 | 0.20 | 0.20 | 0.20 | 0.20 | 0.20 |
| p-Toluylenediamine sulfate | 2.50 | 0.40 | 0.30 | 0.05 | 0.30 | 2.50 | 0.40 | 0.30 |
| RESORCINOL | 0.40 | 0.10 | 1.00 | 0.02 | 0.03 | 0.40 | 0.10 | 1.00 |
| 2,4-diaminophenoxyethanol 2 HCl | 2.00 | — | — | — | — | 2.00 | — | — |
| 2-Methylresorcinol | — | 1.00 | 0.03 | — | 0.50 | — | 1.00 | 0.03 |
| 2,4,5,6-tetraaminopyrimidine sulfate | — | 1.50 | — | — | — | — | 1.50 | — |
| Bis-(5-amino-2-hydroxyphenyl)methane 2 HCl | — | 0.06 | — | — | — | — | 0.06 | — |
| m-Aminophenol | — | — | 0.01 | 0.03 | 0.02 | — | — | 0.01 |
| 4-Chlororesorcinol | — | — | 0.60 | 0.01 | 0.10 | — | — | 0.10 |
| Ascorbic acid | 0.10 | 0.10 | 0.10 | 0.10 | 0.10 | 0.10 | 0.10 | 0.10 |
| Sodium sulfite, 96% | 0.40 | 0.40 | 0.40 | 0.40 | 0.40 | 0.40 | 0.40 | 0.40 |
| PGE-1 | 1.00 | 1.50 | 2.00 | 0.50 | 0.75 | 1.00 | 1.00 | 2.50 |
| Aqua | to 100 | | | | | | | |

TABLE (6)

Coloring Agents

|  | F9 | F10 | F11 | F12 | F13 | F14 | F15 | F16 |
|---|---|---|---|---|---|---|---|---|
| Cetearyl alcohol | 8.00 | 8.00 | 8.00 | 8.00 | 8.00 | 8.00 | 8.00 | 8.00 |
| LOROL | 3.00 | 3.00 | 3.00 | 3.00 | 3.00 | 3.00 | 3.00 | 3.00 |
| EUMULGIN B2 | 2.00 | 2.00 | 2.00 | 2.00 | 2.00 | 2.00 | 2.00 | 2.00 |

TABLE (6)-continued

| Coloring Agents | | | | | | | | |
|---|---|---|---|---|---|---|---|---|
| | F9 | F10 | F11 | F12 | F13 | F14 | F15 | F16 |
| Ascorbic acid | 0.50 | 0.50 | 0.50 | 0.50 | 0.50 | 0.50 | 0.50 | 0.50 |
| Sodium sulfite, 96% | 0.50 | 0.50 | 0.50 | 0.50 | 0.50 | 0.50 | 0.50 | 0.50 |
| TURPINAL SL | 0.20 | 0.20 | 0.20 | 0.20 | 0.20 | 0.20 | 0.20 | 0.20 |
| GLUADIN W 40 | 4.00 | 4.00 | 4.00 | 4.00 | 4.00 | 4.00 | 4.00 | 4.00 |
| Ammonia, 25% | 6.00 | 6.00 | 6.00 | 6.00 | 6.00 | 6.00 | 6.00 | 6.00 |
| RESORCINOL | 0.10 | 8.00 | 8.00 | 8.00 | 8.00 | 8.00 | 8.00 | 8.00 |
| p-Toluylenediamine sulfate | 0.15 | 0.70 | 1.80 | 0.15 | 0.70 | 1.80 | 0.70 | 1.80 |
| 4-Chlororesorcinol | 0.03 | 0.02 | 0.50 | 0.03 | 0.02 | 0.50 | 0.02 | 0.50 |
| 2-Amino-2-methylamino-6-methoxypyridine | 0.01 | — | — | 0.01 | — | — | — | — |
| 2,6-Dihydroxy-3,4-dimethylpyridine | — | 0.02 | — | — | 0.02 | — | 0.02 | — |
| 2,7-Dihydroxynaphthalene | — | 0.01 | — | — | 0.01 | — | 0.01 | — |
| 2-Methylresorcinol | — | 0.05 | — | — | 0.05 | — | 0.05 | — |
| m-Aminophenol | — | 0.10 | — | — | 0.10 | — | 0.10 | — |
| 2,4-Diaminophenoxyethanol 2 HCl | — | 0.01 | — | — | 0.01 | — | 0.01 | — |
| 3-Amino-2-methylamino-6-methoxypyridine | — | 0.01 | 0.10 | — | 0.01 | 0.10 | 0.01 | 0.10 |
| 1,3-Bis-(2,4-diaminophenoxy)propane 4 HCl | — | — | 0.30 | — | — | 0.30 | — | 0.30 |
| PGE-1 | 1.00 | 1.50 | 2.00 | 1.00 | 0.50 | 0.25 | 1.00 | 1.25 |
| Water | | | | to 100 | | | | |

TABLE (7)

| Developers 3.2.2 Developers | | | | | | | | |
|---|---|---|---|---|---|---|---|---|
| | F1 | F2 | F3 | F4 | F5 | F6 | F7 | F8 |
| Dipicolinic acid | 0.10 | 0.10 | 0.10 | 0.10 | 0.10 | 0.10 | 0.10 | 0.10 |
| Disodium pyrophosphate | 0.03 | 0.03 | 0.03 | 0.03 | 0.03 | 0.03 | 0.03 | 0.03 |
| TURPINAL SL | 1.50 | 1.50 | 1.50 | 1.50 | 1.50 | 1.50 | 1.50 | 1.50 |
| TEXAPON NSO UP | 2.00 | 2.00 | 2.00 | 2.00 | 2.00 | 2.00 | 2.00 | 2.00 |
| ACULYN 33A | 12.00 | 12.00 | 12.00 | 12.00 | 12.00 | 12.00 | 12.00 | 12.00 |
| Hydrogen peroxide, 50% | 12.00 | 6.00 | 12.00 | 6.00 | 12.00 | 6.00 | 12.00 | 6.00 |
| Ammonia | 0.62 | 0.62 | 0.62 | 0.62 | 0.62 | 0.62 | 0.62 | 0.62 |
| Water | | | | to 100 | | | | |

TABLE (8)

| Developers | | | | | | | | |
|---|---|---|---|---|---|---|---|---|
| | F9 | F10 | F11 | F12 | F13 | F14 | F15 | F16 |
| LOROL C16 | 3.50 | 3.50 | 3.50 | 3.50 | 3.50 | 3.50 | 3.50 | 3.50 |
| EUMULGIN B2 | 1.00 | 1.00 | 1.00 | 1.00 | 1.00 | 1.00 | 1.00 | 1.00 |

TABLE (8)-continued

| Developers | | | | | | | | |
|---|---|---|---|---|---|---|---|---|
| | F9 | F10 | F11 | F12 | F13 | F14 | F15 | F16 |
| DISPONIL FES 77 IS | 2.50 | 2.50 | 2.50 | 2.50 | 2.50 | 2.50 | 2.50 | 2.50 |
| Hydrogen peroxide, 50% | 24.00 | 20.00 | 12.00 | 24.00 | 20.00 | 12.00 | 24.00 | 20.00 |
| TURPINAL SL | 1.50 | 1.50 | 1.50 | 1.50 | 1.50 | 1.50 | 1.50 | 1.50 |
| ACULYN 33A | 10.0 | 10.0 | 10.0 | 10.0 | 10.0 | 10.0 | 10.0 | 10.0 |
| Water | | | | to 100 | | | | |

The values indicated in Tables (7) and (8) represent weight percentages of the components.

3.3 Ammonia-Free Oxidative Coloring Agents

The coloring agents F17 to F25 are each made up of a color cream and a developer recited below. In order to manufacture the ready-to-use coloring agent, 50 g of the color cream was mixed with 50 g of the developer while stirring. Upon application onto head hair and with a contact time of 30 minutes, an outstanding color result was observed after rinsing and drying. The hair had a well-groomed external appearance and a natural shine, and was easy to comb. The values indicated in Tables (9) and (10) represent weight percentages of the components.

TABLE (9)

| Coloring Agents 3.3.1 Color creams | | | | | | | | | |
|---|---|---|---|---|---|---|---|---|---|
| | F17 | F18 | F19 | F20 | F21 | F22 | F23 | F24 | F25 |
| HYDRENOL D | 7.15 | 7.15 | 7.15 | 7.15 | 7.15 | 7.15 | 7.15 | 7.15 | 7.15 |
| LOROL | 2.60 | 2.60 | 2.60 | 2.60 | 2.60 | 2.60 | 2.60 | 2.60 | 2.60 |
| EUMULGIN B1 | 0.65 | 0.65 | 0.65 | 0.65 | 0.65 | 0.65 | 0.65 | 0.65 | 0.65 |
| EUMULGIN B2 | 0.65 | 0.65 | 0.65 | 0.65 | 0.65 | 0.65 | 0.65 | 0.65 | 0.65 |
| AKYPO Soft 45 NV | 10.0 | 10.0 | 10.0 | 10.0 | 10.0 | 10.0 | 10.0 | 10.0 | 10.0 |
| TEXAPON K 14 S, 70% | 2.80 | 2.80 | 2.80 | 2.80 | 2.80 | 2.80 | 2.80 | 2.80 | 2.80 |
| PLANTACARE 1200 | 2.00 | 2.00 | 2.00 | 2.00 | 2.00 | 2.00 | 2.00 | 2.00 | 2.00 |
| Product W 37194 | 3.75 | 3.75 | 3.75 | 3.75 | 3.75 | 3.75 | 3.75 | 3.75 | 3.75 |
| 2-Aminoethan-1-ol | 3.10 | 2.80 | 2.00 | 3.10 | 2.80 | 2.00 | 3.10 | 2.80 | 2.00 |
| L-Arginine | — | 1.00 | — | — | 1.00 | — | — | 1.00 | — |

TABLE (9)-continued

Coloring Agents
3.3.1 Color creams

| | F17 | F18 | F19 | F20 | F21 | F22 | F23 | F24 | F25 |
|---|---|---|---|---|---|---|---|---|---|
| 2-Amino-2-methylpropanol | — | — | 1.50 | — | — | 1.50 | — | — | 1.50 |
| Sodium chloride | 0.50 | 0.50 | 0.50 | 0.50 | 0.50 | 0.50 | 0.50 | 0.50 | 0.50 |
| Sodium sulfite | 0.40 | 0.40 | 0.40 | 0.40 | 0.40 | 0.40 | 0.40 | 0.40 | 0.40 |
| Ascorbic acid | 0.10 | 0.10 | 0.10 | 0.10 | 0.10 | 0.10 | 0.10 | 0.10 | 0.10 |
| TURPINAL SL | 0.20 | 0.20 | 0.20 | 0.20 | 0.20 | 0.20 | 0.20 | 0.20 | 0.20 |
| Sodium water glass 40/42 | 0.50 | 0.50 | 0.50 | 0.50 | 0.50 | 0.50 | 0.50 | 0.50 | 0.50 |
| Potassium hydroxide, 50% | 1.00 | 1.00 | 1.00 | 1.00 | 1.00 | 1.00 | 1.00 | 1.00 | 1.00 |
| Glycine | 1.00 | 1.00 | 1.00 | 1.00 | 1.00 | 1.00 | 1.00 | 1.00 | 1.00 |
| PGE-1 | 1.00 | 1.00 | 1.00 | 3.00 | 0.50 | 4.50 | 0.45 | 2.00 | 1.00 |
| p-Toluylenediamine sulfate | 0.40 | 0.40 | 0.40 | 0.40 | 0.40 | 0.40 | 0.40 | 0.40 | 0.40 |
| 2,7-dihydroxynaphthalene | 0.03 | 0.03 | 0.03 | 0.03 | 0.03 | 0.03 | 0.03 | 0.03 | 0.03 |
| RESORCINOL | 0.12 | 0.12 | 0.12 | 0.12 | 0.12 | 0.12 | 0.12 | 0.12 | 0.12 |
| 4-Chlororesorcinol | 0.06 | 0.06 | 0.06 | 0.06 | 0.06 | 0.06 | 0.06 | 0.06 | 0.06 |
| 2-Methylresorcinol | 0.02 | 0.02 | 0.02 | 0.02 | 0.02 | 0.02 | 0.02 | 0.02 | 0.02 |
| m-Aminophenol | 0.02 | 0.02 | 0.02 | 0.02 | 0.02 | 0.02 | 0.02 | 0.02 | 0.02 |
| Water | | | | | to 100 | | | | |

TABLE (10)

Developers
3.3.2 Developer

| | |
|---|---|
| Dipicolinic acid | 0.10 |
| Disodium pyrophosphate | 0.03 |
| TURPINAL SL | 1.50 |
| TEXAPON NSO UP | 2.00 |
| ACULYN 33A | 12.00 |
| Hydrogen peroxide, 50% | 12.00 |
| Water | to 100 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An oxidative hair treatment agent comprising, in a cosmetic carrier, a combination of:
    at least one oxidizing agent; and
    at least one modified starch, the modified starch:
        being uncrosslinked;
        being modified by propylene oxide;
        having an average molecular weight between 50 and 2500 kiloDaltons (kDa); and
        having a propylene oxide content between 0.1 and 20.0 weight percent (wt%) based on the weight of the modified starch.

2. The agent of claim 1, in which the at least one modified starch has an average molecular weight between 100 and 2000 kDa.

3. The agent of claim 1, in which the at least one modified starch has an average molecular weight between 500 and 1800 kDa.

4. The agent of claim 1, in which the at least one modified starch has an average molecular weight between 700 and 1000 kDa.

5. The agent of claim 1, in which the at least one modified starch has a propylene oxide content, based on the weight of the modified starch, between 2.0 and 12.0 wt%.

6. The agent of claim 1, in which the at least one modified starch has a propylene oxide content, based on the weight of the modified starch, between 3.0 and 10.0 wt%.

7. The agent of claim 1, in which the at least one modified starch has a propylene oxide content, based on the weight of the modified starch, between 4.0 and 6.0 wt%.

8. The agent of claim 1, in which the at least one modified starch has, in a 43-wt% solution in water, a viscosity between 150 and 1,500,000 millipascal seconds (mPa·s).

9. The agent of claim 1, in which the at least one modified starch has, in a 43-wt% solution in water, a viscosity between 3000 and 200,000 millipascal seconds (mPa·s).

10. The agent of claim 1, in which the at least one modified starch has, in a 43-wt% solution in water, a viscosity between 10,000 and 100,000 millipascal seconds (mPa·s).

11. The agent of claim 1, in which the at least one modified starch has, in a 43-wt% solution in water, a viscosity between 40,000 to 70,000 millipascal seconds (mPa·s).

12. The agent of claim 1, in which the at least one modified starch forms between 0.01 and 20 wt% of the agent.

13. The agent of claim 1, in which the at least one modified starch forms between 0.01 and 10 wt% of the agent.

14. The agent of claim 1, in which the at least one modified starch forms between 0.1 and 5.0 wt% of the agent.

15. The agent of claim 1, in which the at least one modified starch forms between 0.1 and 2.0 wt% of the agent.

16. The agent of claim 1, further comprising a color changing component, in which the color changing component comprises:
    at least one oxidation dye precursor of the developer component type; and
    optionally, at least one coupler component.

17. The agent of claim 1, in which the at least one oxidizing agent comprises at least one of hydrogen peroxide and at least one addition product of hydrogen peroxide with inorganic compounds, organic compounds, or combinations thereof.

18. A method for providing an oxidative treatment to hair, the method comprising:
    applying at least one oxidative cosmetic agent onto hair, in which the oxidative cosmetic agent comprises, in a cosmetic carrier, at least one oxidizing agent;
    rinsing the oxidative cosmetic agent out of the hair after a contact time;

in which the method further comprises at least one of:
(i) immediately before applying the at least one oxidative cosmetic agent onto hair, applying a second cosmetic agent to the hair, and rinsing the second cosmetic agent from the hair, in which the second cosmetic agent comprises, in a cosmetic carrier, at least one modified starch, in which the modified starch:
is uncrosslinked;
has an average molecular weight between 50 and 2500 kiloDaltons (kDa); and
has a propylene oxide content between 0.1 and 20.0 weight percent (wt%), based on the weight of the modified starch; and
(ii) adding at least one modified starch into the oxidative cosmetic agent, in which the modified starch:
is uncrosslinked;
has an average molecular weight between 50 and 2500 kiloDaltons (kDa); and
has a propylene oxide content between 0.1 and 20.0 weight percent (wt%), based on the weight of the modified starch.

19. A method for using at least one modified starch to decrease oxidative hair damage in the context of an oxidative hair treatment, the method comprising:
applying the at least one modified starch to hair, the modified starch:
being uncrosslinked;
being modified by propylene oxide;
having an average molecular weight between 50 and 2500 kiloDaltons (kDa); and
having a propylene oxide content between 0.1 and 20.0 weight percent (wt%), based on the weight of the modified starch; and
rinsing the modified starch from the hair;
in which the oxidative hair treatment is a composition to be applied to hair that comprises at least one oxidizing agent.

* * * * *